United States Patent [19]
Johnson et al.

[11] Patent Number: 5,655,545
[45] Date of Patent: *Aug. 12, 1997

[54] DISSECTION OF TISSUE BY TISSUE EXPANDER

[76] Inventors: Gerald W. Johnson, 16000 Steubner Airline, Suite 105, Spring (Houston), Tex. 77379; Jeffrey W. Johnson, 326 Hillside Cir., West Monroe, La. 71291

[ * ] Notice: The term of this patent shall not extend beyond the expiration date of Pat. No. 5,258,026.

[21] Appl. No.: 419,384

[22] Filed: Mar. 30, 1995

Related U.S. Application Data

[60] Continuation-in-part of Ser. No. 134,629, Oct. 12, 1993, abandoned, which is a division of Ser. No. 832,072, Feb. 6, 1992, Pat. No. 5,258,026.

[51] Int. Cl.$^6$ .................................................... A61B 19/00
[52] U.S. Cl. ............................................................ 128/898
[58] Field of Search ..................................... 128/897, 898; 606/191, 192, 198; 623/7, 8

[56] References Cited

PUBLICATIONS

Gaur, Laparoscopic Operative Retroperitoneoscopy: Use of a New Device., The Journal of Urology, pp.1137–1139. Oct. 1992.

*Primary Examiner*—Lee S. Cohen
*Assistant Examiner*—Samuel Gilbert
*Attorney, Agent, or Firm*—Neal J. Mosely

[57] ABSTRACT

A surgical procedure for tissue dissection is disclosed in which an incision is made in a human body. A hollow tissue expander is then inserted into the incision to a point where a space or cavity or pocket is desired. Fluid is forced into the expander to cause it to expand an separate two layers of tissue to form the space or cavity or pocket. The expander can be used to dissect or create spaces: (1) within subcutaneous fat; (2) between skin and bone; skin and muscle or skin and fascia; (3) between fat and bone; fat and muscle; fat and fascia; (4) between peritoneum and muscle; peritoneum and fascia; (5) between bladder and other tissue; (6) between nerves and other tissue; (7) between blood vessels and other tissues; (8) between muscle and other tissues. The tissue expander can, in fact, be used any place in the body where a surgeon could or would use other instruments to create spaces in, dissect or separate soft tissues. This use of a tissue expander to dissect tissue, create cavities or pockets, or separate layers of soft tissue can be done: (1) under direct vision; (2) under endoscopic vision; (3) under X-ray vision; (4) under blind conditions by manual palpatation; (5) or any combination of the above.

9 Claims, 5 Drawing Sheets

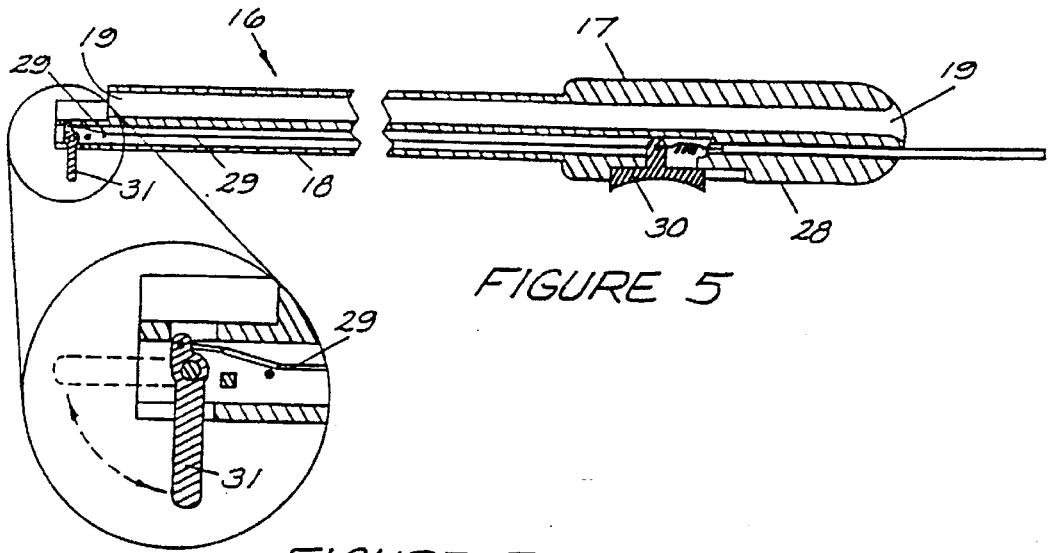
FIGURE 5
FIGURE 5A
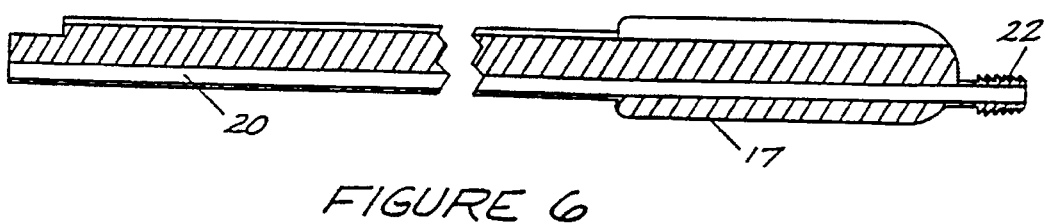
FIGURE 6
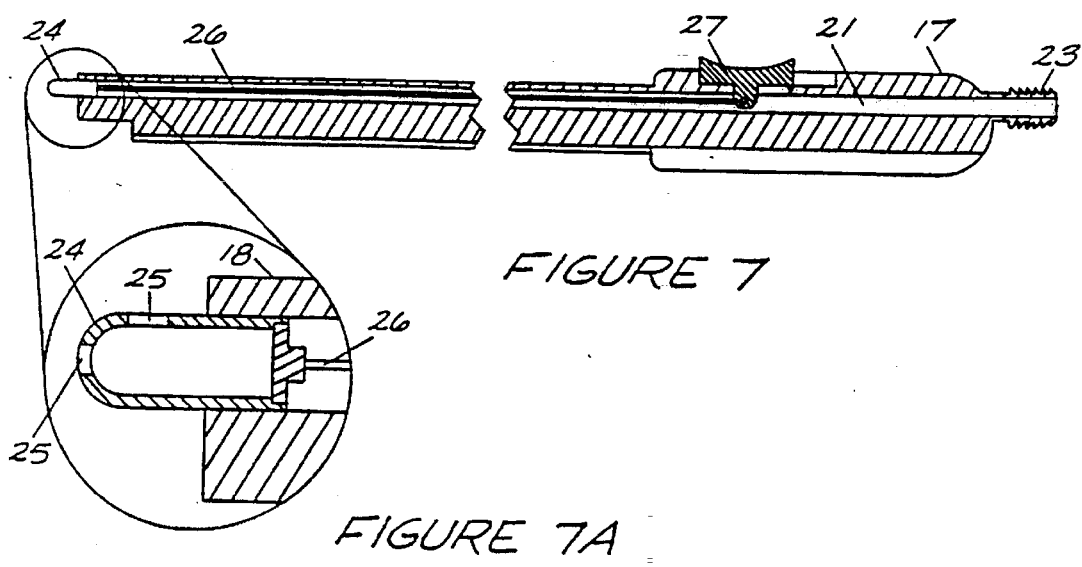
FIGURE 7
FIGURE 7A

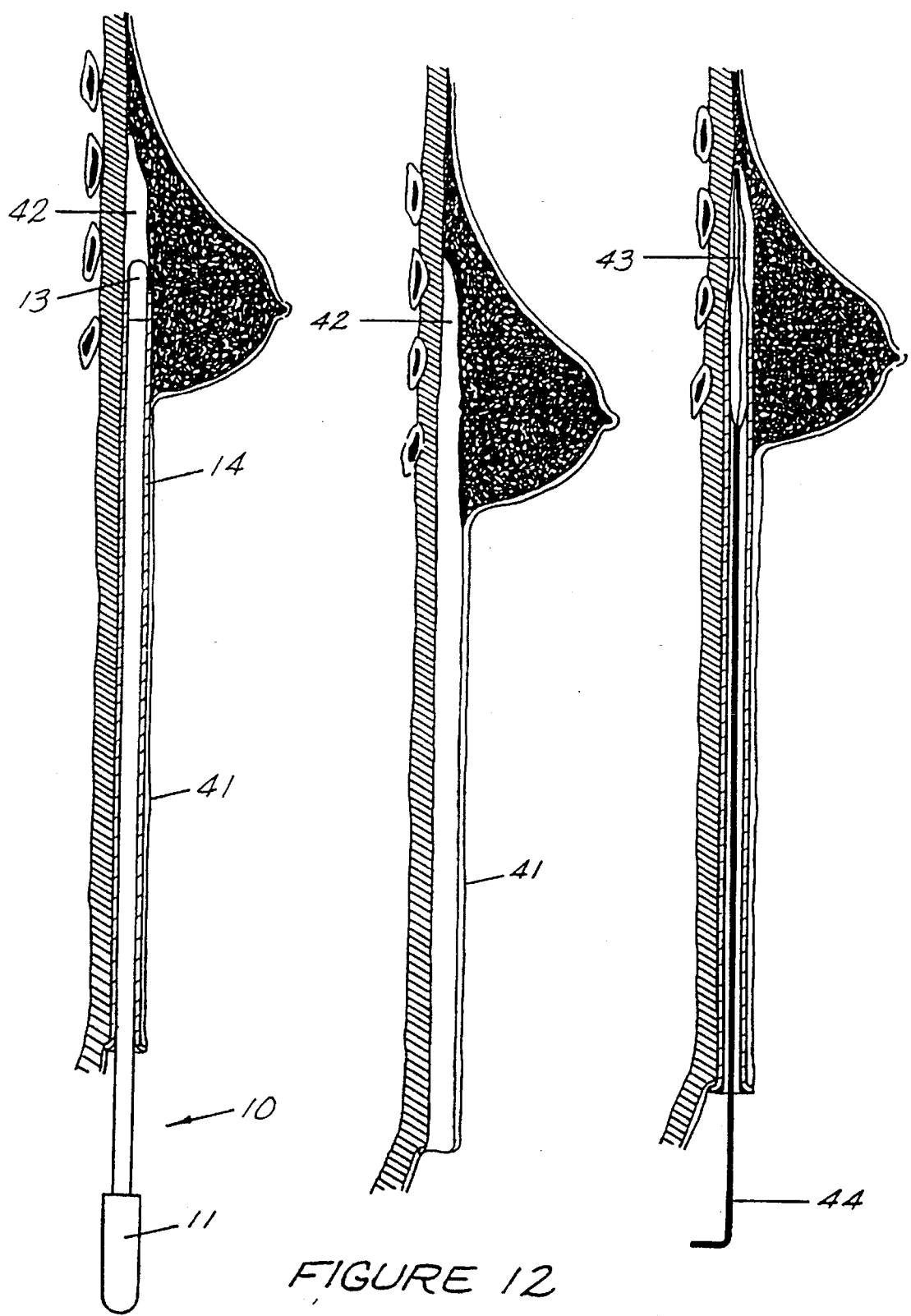

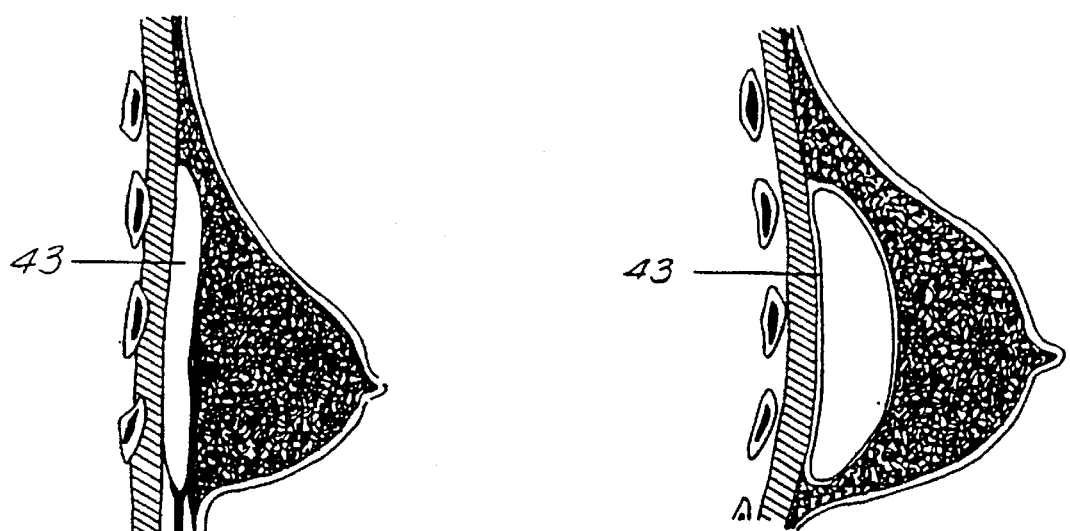
FIGURE 15
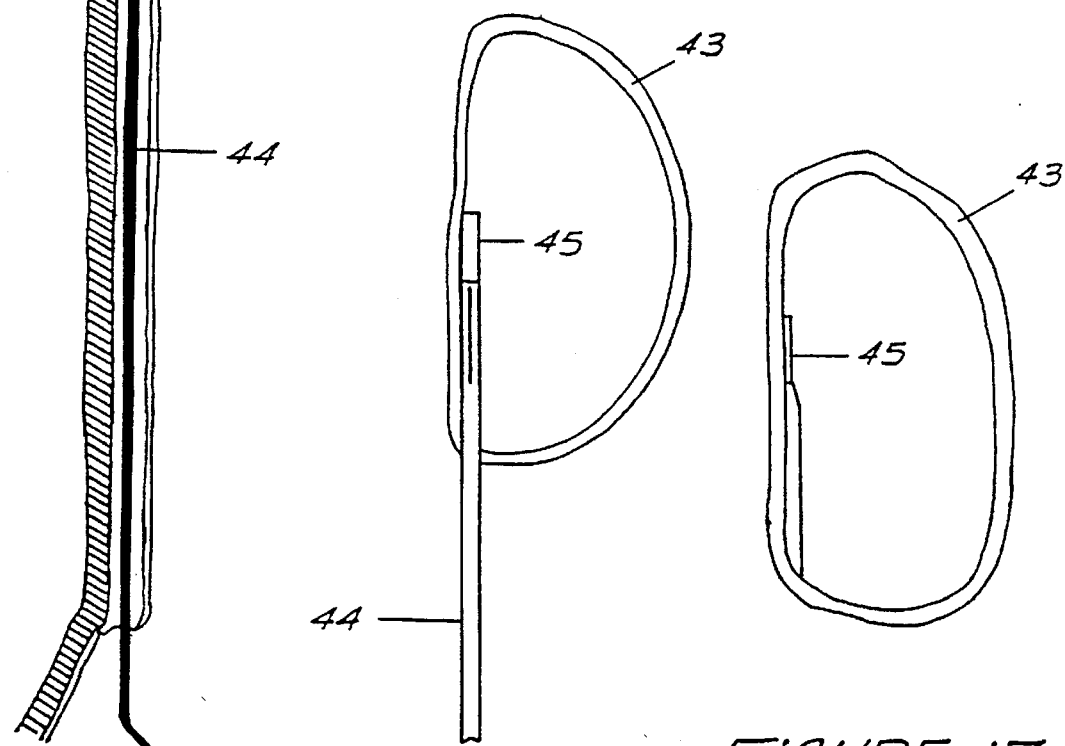
FIGURE 16
FIGURE 17
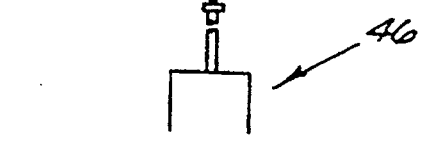
FIGURE 14

1

DISSECTION OF TISSUE BY TISSUE EXPANDER

CROSS REFERENCE TO RELATED APPLICATION

This application is a continuation-in-part of application Ser. No.: 08/134,629, filed Oct. 12, 1993, now abandoned, which is a division of Ser. No. 832,072 filed Feb. 6, 1992, now U.S. Pat. No. 5,258,026 issued Nov. 2, 1993.

BACKGROUND OF THE INVENTION

1. Field of the Invention

This invention relates to new and useful improvements in surgical procedures for opening a space or cavity in a human body.

2. Brief Description of the Prior Art

In the medical literature, surgical creation of a space, cavity or pocket, in the human body, e.g., subglandular or in the submuscular location, involves two basic techniques, each technique utilizing two skin incisions. The two techniques are the blunt dissection and the sharp dissection technique.

The blunt dissection technique, in breast surgery, involves gaining access to the breast through a skin incision. The surgeon then identifies the location (subglandular or submuscular) and, using a finger or other blunt surgical instrument, the breast is bluntly separated from the pectoralis muscle fascia (to create the subglandular pocket) or the pectoralis major muscle is bluntly separated from the chest wall (to create the submuscular pocket). The blunt dissection technique is usually done "blindly" not under direct vision.

The sharp dissection technique involves gaining access to the breast through a skin incision. The surgeon then uses a knife, scissors, electrocautery, or laser to dissect the subglandular or submuscular pocket. The sharp dissection technique is almost always done under direct vision.

The blunt dissection technique generally causes more bleeding and bruising, and after blunt dissection may surgeons will then use direct vision and cautery or laser to control any blood vessels that are bleeding.

Many surgeons will also use a combinations of the blunt dissection and sharp dissection techniques to create the pocket for the implant devices.

In Johnson U.S. Pat. No. 5,250,072, a tissue dissection is made to form a pocket for receiving an breast implant in which an incision is made into the body and a hollow tissue expander is inserted and expanded to dissect tissue.

SUMMARY OF THE INVENTION

One of the objects of this invention is to provide a new and improved surgical procedure for dissecting tissue to form a space or cavity or pocket.

Another object of this invention is to provide a new and improved procedure in which there is minimal bleeding, bruising and swelling as a result of the "tissue expansion" technique to dissect the pocket, as opposed to the sharp and/or blunt techniques of dissection presently used.

Another object of this invention is to provide a new and improved procedure for tissue dissection in which there is much less damage to nerves than caused by other techniques currently used.

Another object of this invention is to provide a new and improved surgical procedure for tissue dissection and instruments which permit the direct, undistorted visualization of the site during the operation.

Still another object of this invention is to provide a new and improved surgical procedure for tissue dissection in which an incision is made into the body where the surgeon wants to create a space or cavity or pocket and a hollow tissue expander is inserted and expanded by application of fluid to dissect the tissue.

Other objects of the invention will become apparent from time to time throughout the specification and claims as hereinafter related.

BRIEF DESCRIPTION OF THE DRAWINGS

FIG. 5 is a sectional view taken on the section lines 5—5 of FIG. 4 showing the electrosurgical and electrocauterizing and endoscopic viewing portions of the instrument.

FIG. 5A is a detail view, slightly enlarged, of the electrosurgical or electrocauterizing head of the instrument.

FIG. 6 is a sectional view taken on the section lines 6—6 of FIG. 4 showing the irrigation portion of the instrument.

FIG. 7 is a sectional view taken on the section lines 7—7 of FIG. 4 showing the suction portion of the instrument.

FIG. 7A is a detail view, slightly enlarged, of the adjustable suction tip on the instrument.

FIG. 11 is a sectional view of a female torso, including the rib cage and the breast between the breast tissue and muscle showing the endotube and obturator of FIG. 1 inserted beneath the breast to form a pocket to receive a prosthesis according to a preferred embodiment of this invention.

FIG. 12 is a sectional view of a female torso, including the rib cage and the breast, as in FIG. 11, showing the endotube and obturator removed to form a pocket to receive a prosthesis and a tunnel for insertion thereof according to a preferred embodiment of this invention.

FIG. 13 is a sectional view of a female torso, including the rib cage and the breast showing the endotube and a breast prosthesis carried thereon inserted beneath the breast in the pocket formed in a previous step in the procedure and showing the prosthesis fill tube extending from the end of the endotube.

FIG. 14 is a sectional view of a female torso, including the rib cage and the breast, as in FIG. 13, showing the endotube removed and a breast prosthesis inserted beneath the breast in the pocket formed in a previous step in the procedure and showing the prosthesis fill tube connected to a pump for filling the prosthesis.

FIG. 15 is a sectional view on the female breast showing the prosthesis filled and in place.

FIG. 16 is a sectional view of the breast prosthesis with a fill tube in place for filling.

FIG. 17 is a sectional view of the breast prosthesis with the fill tube removed and the fill valve closed after filling.

DESCRIPTION OF THE PREFERRED EMBODIMENTS

Dissection by Use of Tissue Expander

Figure 1:
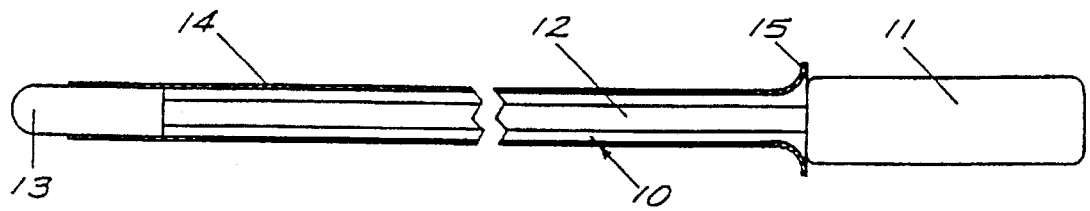
FIG. 1 is a view, partly in section, of an endotube and obturator for use in an endoscopic breast mammoplasty according to a preferred embodiment of this invention.
Figure 2:
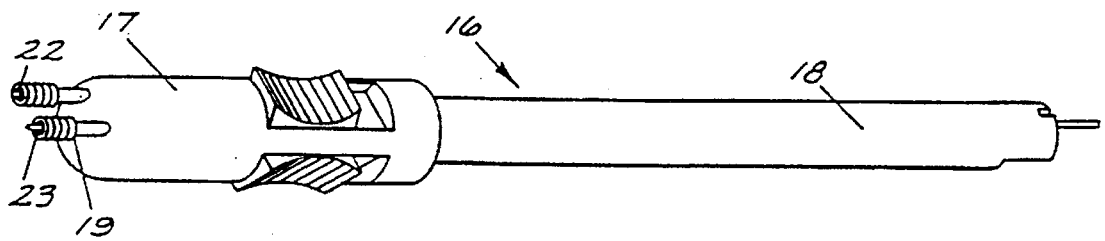
FIG. 2 is an isometric view from one end of an electrosurgical instrument, for insertion through the endotube shown in FIG. 1, having provision for electrosurgery or electrocauterization, irrigation and vacuum, and endoscopic viewing according to a preferred embodiment of this invention.
Figure 3:
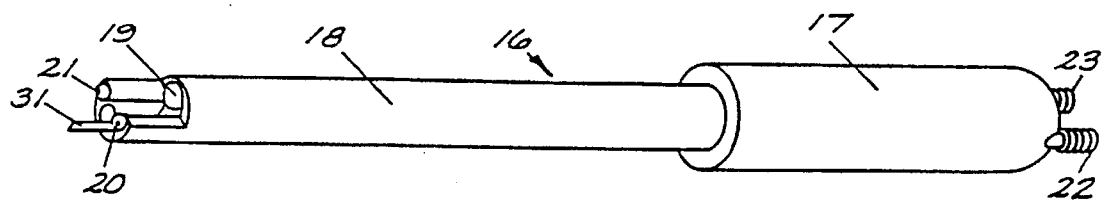
FIG. 3 is an isometric view from the other end of the electrosurgical instrument shown in FIG. 2, for insertion through the endotube shown in FIG. 1, having provision for electrosurgery or electrocauterization, irrigation and vacuum, and endoscopic viewing according to a preferred embodiment of this invention.
Figure 4:
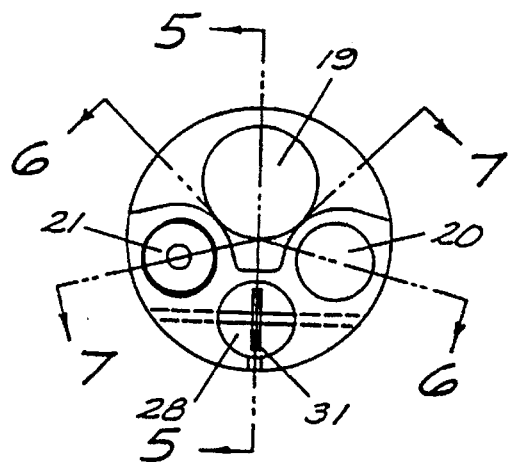
FIG. 4 is an end elevation from the left end of the instrument as shown in FIG. 3.

A tissue dissection is accomplished by a surgeon making a remote incision into the body and inserting a hollow tissue expander into the incision to a point where a space or cavity or pocket is desired. Fluid is then forced into the expander to cause it to expand and separate two layers of tissue to form the space or cavity or pocket. The dissection takes place along the edges of the incision and peripherally outward from the tissue expander.

The expander can be used to dissect or create spaces:

(1) within subcutaneous fat;

(2) between skin and bone; skin and muscle or skin and fascia;

(3) between fat and bone; fat and muscle; fat and fascia;

(4) between peritoneum and muscle; peritoneum and fascia;

(5) between bladder and other tissue;

(6) between nerves and other tissue;

(7) between blood vessels and other tissues;

(8) between muscle and other tissues.

The tissue expander can, in fact, be used any place in the body where a surgeon could or would use other instruments to create spaces in, dissect or separate soft tissues. The term dissection of tissue, as used herein, encompasses all of the tissue separations or dissections listed above.

This use of a tissue expander to dissect tissue, create cavities or pockets, or separate layers of soft tissue can be done:

(1) under direct vision;

(2) under endoscopic vision;

(3) under X-ray vision;

(4) under blind conditions by manual palpitation;

(5) or any combination of the above.

This use of the tissue expander in an operation as a dissecting tool is a new concept as described in Johnson U.S. Pat. No. 5,250,072 and is not related to older techniques of tissue expansion where a tissue expander has been implanted in a body by surgery and expanded periodically over an extended period of time, viz., weeks or months.

The description of breast surgery given below is a special case of the use of a hollow, expandable tissue expander for tissue dissection and the formation of a space, cavity or pocket.

The Surgical Instruments

Referring to the drawings by numerals of reference, and more particularly to FIGS. 1–8, there are shown the improved surgical instruments forming a preferred embodiment of this invention and used in the method of endoscopic breast augmentation mammoplasty as described hereinafter. In the description of these instruments, the materials of construction and dimensions are somewhat critical for obtaining the desired results in breast augmentation surgery.

An obturator 10 (FIG. 1) comprises a handle 11, rod 12, and bullet-shaped nose piece 13, preferably formed of surgical stainless steel or plastic of satisfactory strength. The obturator (or trocar) is shown in position fully inserted inside a hollow endotube 14 which is open at beth ends and has a flared end portion 15 adjacent to handle 11. Both the endotube 14 and obturator 10 are preferably formed of surgical grade stainless or plastic of satisfactory strength steel. While surgical steel is preferred for instruments having long life, it may be desirable to make the instruments of a sterile plastic which may be disposed of after each operation.

The obturator 10 is about 24" long including the handle 11 and the bullet shaped nose piece 13 is sized for a sliding fit inside endotube 14. The endotube 14 is about 16" long, having an I.D. of 0.70" and O.D. of 0.73". Smaller sizes may be used if desired. When the obturator 10 is assembled in the endotube 14, the distance from the flared end 15 to the end of bullet-shaped nose piece 13 is about 18".

The dimensions are chosen to fit the requirements of the surgery. The length required is sufficient to extend from the navel to a point behind the breast of the surgical patient. Different lengths may be required for different sizes of patients. The diameter of the endotube 14 and obturator 10 are chosen to provide an opening large enough for the surgical instruments which are to be introduced through the endotube 14 without being so large that excessive trauma is produced by the surgical procedure.

In FIGS. 2–7A, there is shown a combined instrument for irrigation, application of vacuum, electrocutting and electrocauterization, or fiberoptic laser operation, and endoscopic viewing. The electrosurgical instrument 16 (FIGS. 2 and 3), preferably formed of surgical stainless steel or a hard plastic such as polyurethane or polycarbonate, comprises a handle 17 and body portion 18. The instrument 16 is of sufficient length to extend through and out of the end of endotube 14 during use and body portion 18 has a diameter permitting a sliding fit therein.

Instrument 16 has a longitudinal passage 19 (FIGS. 2–5) for receiving an endoscope during use to observe the site of the surgery. Instrument 16 also has passages 20 (FIG. 6) and 21 (FIG. 7) for irrigation and suction. These passages may be combined into a single passage, if desired. Passage 20 has an inlet fitting 22 for connection to an irrigation tube. Passage 21 has an inlet fitting 23 for connection to vacuum for suctioning the surgical site. A hollow suction tip 24, with apertures 25, is positioned in the outlet end of passage 21 and slidable therein for longitudinal extension and retraction by an operating rod 25 movable by actuating lever 26 pivoted in handle 17.

Instrument 16 has a longitudinal passage 28 in which there is positioned a blade electrode 31 for electrocutting or cauterization. An electrode actuating lever 30 on handle 17 is connected remote linkage 29 (of hard conductive steel) to extend or retract blade 31. The distal end of linkage 29 has a movable blade tip 31 pivoted thereon. Extension and retraction of blade linkage 29 by lever 30 is operable to pivot tip 31 inwardly and outwardly to permit cutting and cauterization in an area defined by a circle having the radius of cutting tip 31. Instrument 16 may have a laser cutting and cauterizing element (same as 31) substituted for electric current which would have a deflectable end portion performing the function of cutting tip 31 by inward and outward deflection, according to movement of 31 by lever 30 and linkage 29.

Figure 8:
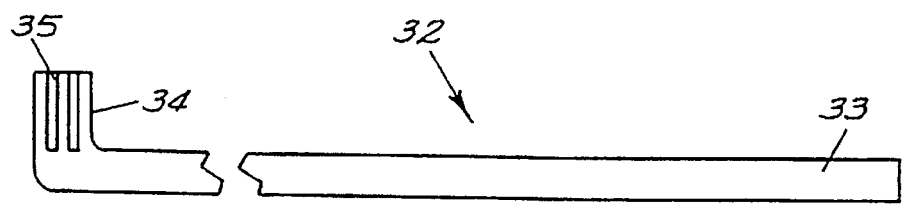
FIG. 8 is a plan view of a dissector used in separating tissue in the endoscopic breast augmentation mammoplasty according to a preferred embodiment of this invention.

In FIG. 8, there is shown a dissector 32 for blunt dissection of tissue in the procedure described below. Dissector 32 has a handle 33 at one end and bent portion 34 at the other end. Bent portion 34 has a plurality of grooves 35 cut therein with sharp edges to facilitate dissection during the surgical procedure.

Surgical Procedure for Endoscopic Breast Augmentation Mammoplasty

This surgical procedure is a totally new and innovative combination of techniques for augmentation of the female breast. All procedures (shown in FIGS. 9–17) were performed under general anesthesia.

Figure 9:
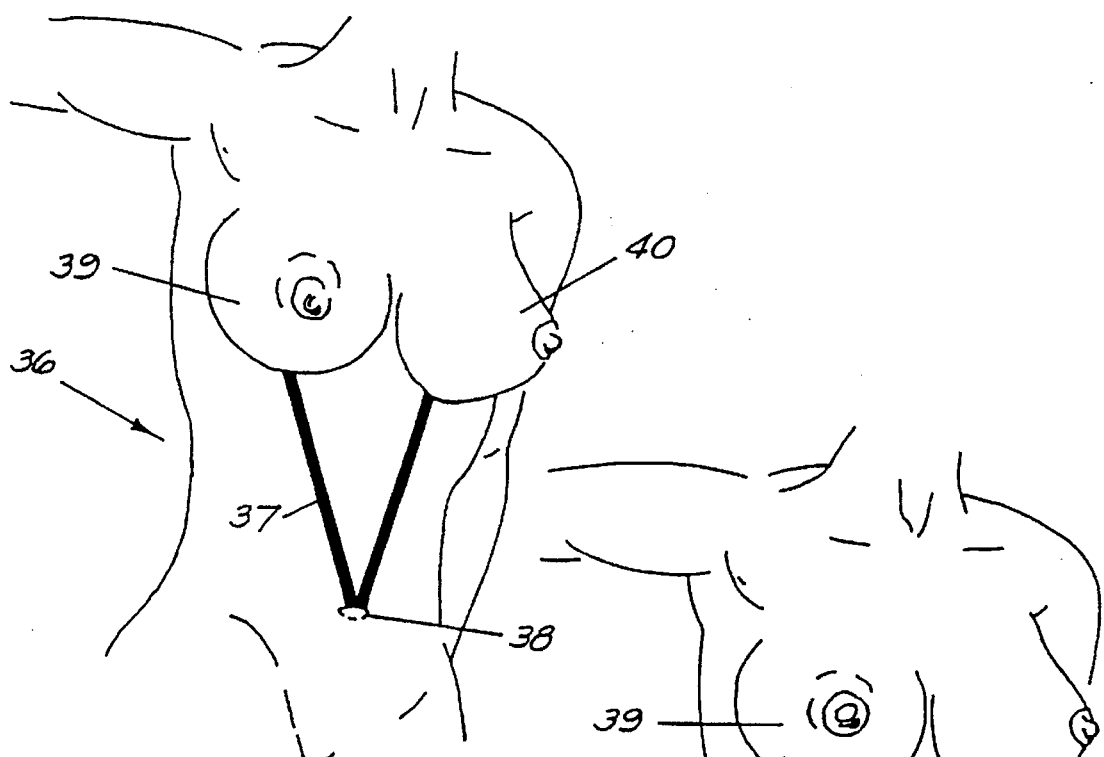
FIG. 9 is a schematic view of a female torso with markings from the navel to the breasts for guidance of the surgeon in carrying out an endoscopic breast augmentation mammoplasty and a navel incision made according to a preferred embodiment of this invention.
Figure 10:
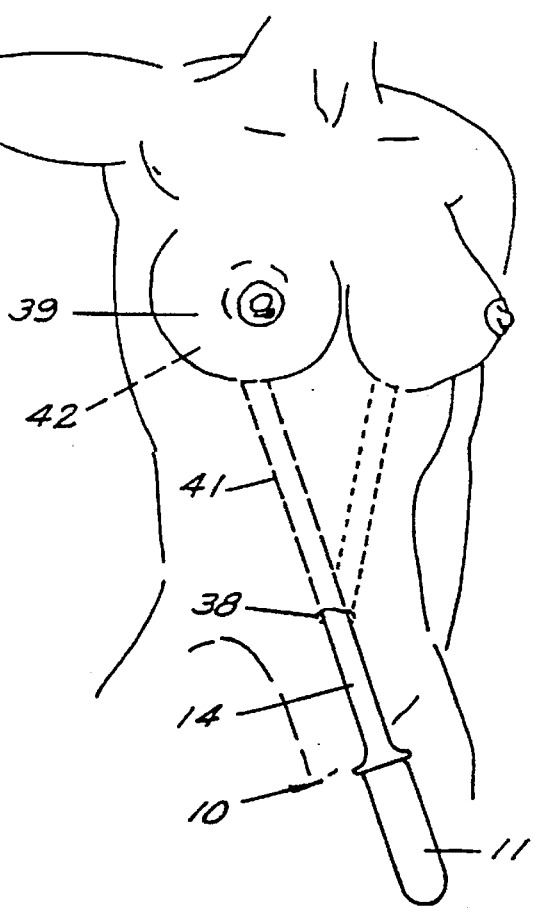
FIG. 10 is a schematic view of a female torso, as in FIG. 9, with markings from the navel to the breasts for guidance of the surgeon in carrying out an endoscopic breast augmentation mammoplasty and showing the endotube and obturator of FIG. 1 partially inserted toward the right breast according to a preferred embodiment of this invention.

A female patient 36 is placed on the operating table and marks 37 made extending from the navel 38 to right breast 39 and left breast 40 in preparation for surgery (FIG. 9). An incision is made inside the navel 38 to commence the surgical procedure.

Endotube 14 and obturator 10 with a bullet shaped nose 13 (assembled as in FIG. 1) is introduced (FIG. 10) into this incision and is passed from the umbilicus, staying just above the fascia of the interior abdominal and chest wall, and below the subcutaneous tissue and fat, to a position just medial to the nipple and 6 to 8 centimeters above the level of the nipple. This movement produces a tunnel 41 leading to breast 39 and a space 42 behind the breast which is ultimately expanded into a pocket for a breast prosthesis or implant.

As the endotube 10 (and obturator 14) is pushed over the inferior margin of the rib cage the operator manipulates the tube 14 with one hand and the breast with the other hand to keep the tube 14 below the breast tissue, but above the pectoralis muscle fascia, if the operator wishes to place the implant in the subglandular or submammary position. If the operator wishes to place the implant submuscular then the endotube 14 and breast are manipulated in order to allow penetration of the pectoralis muscle fibers and direct the endotube to a submuscular position. The formation of the tunnel 41 and space 42 are as shown in FIGS. 11 and 12.

The obturator 10 is then removed and the endoscope is introduced to verify position of the tunnel 41 and to inspect for bleeding. If bleeding is encountered or if further cutting or cauterization is required, the instrument 16 is intro-duced through endotube 14 and the cutting or cauterization car-ried out by blade 29 and cutting tip 31. The space or cavity 42 is irrigated through fitting 22 and passage 20. The cavity 42 is aspirated by suction applied through fitting 23, passage 21 and tip 24.

The endoscope and endotube 14 are then both withdrawn. A device which is an inflatable prosthesis or tissue expander 43 (FIGS. 13 and 15–17) is completely evacuated of air and rolled up tightly. If the fill tube 44 on the device 43 is considered to be in the 6 o'clock position, from the 3 o'clock position the device is rolled up to the midline, then from the 9 o'clock position the other half of the device is rolled up to the midline.

With the device 43 tightly rolled in this fashion, the fill tube 44 of the device is then passed through the endotube 14 from the front end of the endotube, coming out the back end. The device 43 is then partially introduced into the end of the endotube 14 (FIG. 13).

At this point, the device 43 is introduced into the tunnel 41 initially formed by the endotube 14 and is pushed through tunnel 41 to its position in space 42 beneath the breast. The device 43 is held manually by the operator by squeezing the breast and the endotube 14 is then withdrawn to leave the device in place with the fill tube 44 coming out through tunnel 41. Fill tube 44 of the device 43 is connected to a syringe or other device 46 (FIG. 14) that fills the device with sterile physiologic saline.

Whatever the final volume of the device is intended to be, it is overfilled by a volume that is 50% greater than the intended final volume (FIG. 15). As the device is being inflated and overexpanded the surgeon holds pressure and releases pressure in the appropriate manner to shape and form the pocket from space 42 as it is being created by the inflation/expansion of the device.

The same procedure is done for the opposite breast 40.

Attention is turned back to the first breast 39 and the total volume is removed. The device 43 is removed. Any FDA approved mammary implant having the desired structure may be inserted and inflated to the desired volume. One such implant that has proven satisfactory is the RTV SALINE-FILLED MAM-MARY Device manufactured by McGhan Medical Corporation.

The same procedure is repeated for the opposite breast.

Using the endoscope, both breasts 39 and 40 are then inspected to be certain there is no pooling of saline to indicate a problem with a prosthesis and there is no excessive bleeding, and the valve of each implant is inspected to ascertain its integrity.

In the procedure just described, the implant can function as a tissue dissector to separate tissue and form the desired cavity or pocket behind the breast.

A "Y" tipped dissector (not shown) may be used to release any muscular or fibrous bands in the upper part of the breast pocket 42 that could not be released by expansion of the device (tissue expander) 43 or manipulations by the surgeon. A "hockey stick" dissector 32 may be used to release muscular or fibrous bands in the lower portion of the breast pocket 42.

Both the "Y" tipped and "hockey stick" dissector 32 provide methods of blind-blunt dissection. The instrument 16 comprising an electrocautery endopod or a laser endoped, each containing a suction tube, irrigation tube and a small caliber endoscope plus the flexible or movable electrocautery tip or fiberoptic laser tip may be used for sharp dissection under direct vision or coagulation of a bleeding vessel under direct vision.

At the conclusion of the procedure, the umbilical incision 38 is then sutured and a cotton ball put in place and taped and a bandage applied to the breast. The patient can go home directly from the recovery room without requiring hospitalization.

Advantages of this procedure over prior and current surgical procedures for breast augmentation are:

1. Only one incision, in most cases, is required to operate on both breasts (except where an axillary approach is used and two incisions are required).

2. The resultant scar, in most cases, is not on the breasts and is virtually invisible down inside the umbilicus, when an umbilical approach is used.

3. There is minimal bleeding, bruising and swelling as a result of the "tissue expansion" technique, i.e., expansion of tissue expander or prosthesis 43, to form the pocket, as opposed to the sharp and/or blunt techniques of dissection presently used. The dissection takes place along the edges of the incision and peripherally outward from the tissue expander.

4. There is much less damage to nerves than is caused by other techniques currently used.

The results of this new and improved endoscopic breast augmentation mammoplasty were evaluated on the basis of twenty-five cases during November-December 1991.

While this invention has been described fully and completely, it should be understood that, within the scope of the appended claims, the invention may be practiced otherwise than as specifically described.

We claim:

1. A method of surgical dissection of body tissue comprising the steps of making an incision into a body to a point where tissue dissection is needed, providing an inflatable hollow member having an elongated filling tube, inserting said hollow member into said incision to said point where tissue dissection is needed, filling said hollow member with fluid to expand the member to a size greater than said incision to separate and dissect said body tissue along the edges of said incision and peripherally outward from said hollow member and removing the hollow member on completion of surgery.

2. A surgical method according to claim 1 in which said incision is made and said tissue expander is positioned so that expansion of said tissue expander is effective to create spaces, cavities or pockets in the body or to dissect or separate soft tissues in bodily regions selected from the group consisting of:

(a) within subcutaneous fat;

(b) between skin and bone; skin and muscle or skin and fascia;

(c) between fat and bone; fat and muscle; fat and fascia;

(d) between peritoneum and muscle; peritoneum and fascia;

(e) between bladder and other tissue;

(f) between nerves and other tissue;

(g) between blood vessels and other tissues; and (h) between muscle and other tissues.

3. A surgical method according to claim 1 in which the dissection by the tissue expander is carried out under at least one of the conditions selected from the group consisting of (a) direct vision;

(b) endoscopic vision;

(c) X-ray vision; and (d) blind conditions by manual palpitation.

4. A method of surgical dissection of body tissue comprising the steps of making an incision into a body to a point where tissue dissection is needed, providing an inflatable hollow member having an elongated filling inserting said hollow member into said incision to said point where tissue dissection is needed, filling said hollow member with fluid, palpitating the body over said inserted hollow member during filling while palpitating the body over said inserted hollow member to enlarge the inner end of said incision into a pocket.

5. A method of surgical dissection of body tissue comprising the steps of making an incision into a body to a point where tissue dissection is needed, providing an endotube and an obturator having a bullet-shaped nose piece, placing said obturator inside said endotube with said nose piece protruding from the end thereof, providing an inflatable hollow member having an elongated filling tube, inserting said endotube and protruding obturator nose piece through said incision and forcing them into said incision to form a tunnel extending to a space in said tissue comprising said point where tissue dissection is needed, removing said endotube and obturator from said tunnel, placing said hollow member at least partially inside one end of said endotube with said filling tube extending out another end thereof, forcing said hollow member and endotube through said tunnel to said space in said tissue, holding said hollow member in said body space and removing said endotube from said tunnel, and filling said hollow member with fluid to expand the member to separate and dissect said body tissue after removal of said endotube.

6. A surgical method according to claim 5 including the step of palpitating said body during filling said hollow member to enlarge said space into a body pocket.

7. A surgical method according to claim 5 which includes removing said obturator from said endotube after formation of said tunnel and inserting an endoscope, viewing the interior of said tunnel, and moving said endotube, as needed, to adjust the position of said tunnel.

8. A surgical method according to claim 5 including overfilling said hollow member with saline solution by a substantial amount, manually manipulating said body during filling to open a pocket, and subsequently relieving said hollow member of excess liquid before removing said filling tube.

9. A surgical method according to claim 5 including overfilling said hollow member with saline solution by about 50%, manually manipulating said body during filling to open a pocket, and subsequently relieving said hollow member of excess liquid before removing said filling tube.

* * * * *